(12) United States Patent
Dänike et al.

(10) Patent No.: US 11,439,509 B2
(45) Date of Patent: Sep. 13, 2022

(54) INTERIM JOINT PROSTHESIS

(71) Applicant: Waldemar Link GmbH & Co. KG, Hamburg (DE)

(72) Inventors: Andreas Dänike, Henstedt-Ulzburg (DE); Günther Jendro, Kaltenkirchen (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 0 days.

(21) Appl. No.: 15/550,327

(22) PCT Filed: Feb. 12, 2016

(86) PCT No.: PCT/EP2016/053010
§ 371 (c)(1),
(2) Date: Aug. 10, 2017

(87) PCT Pub. No.: WO2016/128551
PCT Pub. Date: Aug. 18, 2016

(65) Prior Publication Data
US 2018/0296352 A1    Oct. 18, 2018

(30) Foreign Application Priority Data
Feb. 13, 2015   (DE) .......................... 102015202715.5

(51) Int. Cl.
*A61F 2/36*    (2006.01)
*A61F 2/38*    (2006.01)
(Continued)

(52) U.S. Cl.
CPC .......... *A61F 2/3662* (2013.01); *A61F 2/3607* (2013.01); *A61F 2/3859* (2013.01);
(Continued)

(58) Field of Classification Search
CPC .. A61F 2002/3664–3668; A61F 2/3859; A61F 2/30734; A61F 2/3607;
(Continued)

(56) References Cited

U.S. PATENT DOCUMENTS 5,458,651 A * 10/1995 Lawes ................. A61F 2/30724
623/23.15
2010/0217401 A1   8/2010 De Beaubien
(Continued)

FOREIGN PATENT DOCUMENTS

| EP | 2 826 445 A1 | 1/2015 |
|---|---|---|
| RU | 138603 U1 | 3/2014 |
| RU | 145177 U1 | 9/2014 |

OTHER PUBLICATIONS

Russia Search Report—RU 2017131848 (dated Jun. 13, 2018).
(Continued)

*Primary Examiner* — William H Matthews
(74) *Attorney, Agent, or Firm* — Chiesa Shahinian & Giantomasi PC (57) ABSTRACT

The invention relates to a modular interim joint prosthesis that can be inserted into a long bone, for replacing an explanted joint endoprosthesis, wherein the interim joint prosthesis has a main body having a main-body coupling segment and has a shaft having a shaft coupling segment and the shaft coupling segment can be detachably coupled to the main-body coupling segment.

9 Claims, 6 Drawing Sheets

(51) Int. Cl.
*A61F 2/30* (2006.01)
*A61F 2/46* (2006.01)

(52) U.S. Cl.
CPC .............. *A61F 2002/30332* (2013.01); *A61F 2002/30405* (2013.01); *A61F 2002/30426* (2013.01); *A61F 2002/30507* (2013.01); *A61F 2002/30604* (2013.01); *A61F 2002/30672* (2013.01); *A61F 2002/30677* (2013.01); *A61F 2002/30881* (2013.01); *A61F 2002/30932* (2013.01); *A61F 2002/3674* (2013.01); *A61F 2002/4638* (2013.01); *A61F 2310/00017* (2013.01); *A61F 2310/00023* (2013.01); *A61F 2310/0052* (2013.01); *A61F 2310/0088* (2013.01)

(58) Field of Classification Search
CPC .... A61F 2/3662; A61F 2/3672; A61F 2/3676; A61F 2/4003; A61F 2/4059; A61F 2002/3674; A61F 2002/30329; A61F 2002/30881; A61F 2002/30884; A61F 2002/4062–4077
See application file for complete search history.

(56) References Cited

U.S. PATENT DOCUMENTS

| | | |
|---|---|---|
| 2014/0194811 A1 | 7/2014 | Barsoum et al. |
| 2014/0277532 A1* | 9/2014 | Teeny .................... A61F 2/38 623/20.24 |
| 2014/0309745 A1 | 10/2014 | Burnikel |
| 2015/0018832 A1 | 1/2015 | Vogt |

OTHER PUBLICATIONS

International Search Report and Written Opinion dated May 23, 2016, in connection with International Patent Application No. PCT/EP2016/053010, filed Feb. 2, 2016, 15 pgs (including translation).

* cited by examiner

Fig. 8 ural patient. This has a negative effect, particularly in the case of a longer dwell time of the spacer in the patient from several weeks to months.

INTERIM JOINT PROSTHESIS

TECHNICAL FIELD

The present invention relates to a modular interim joint prosthesis that can be inserted into a long bone.

PRIOR ART

Owing to the high reliability of joint endoprostheses, in particular in the area of the hip and the knee, their insertion is now a common procedure. However, it can occur that inflammation develops in the area of an implanted endoprosthesis for various reasons. Such a so-called sepsis may necessitate a revision of the previously implanted endoprosthesis. The same also applies in the case of tissue proliferation, e.g. a tumour. In other words, the joint implant located in the body is removed again because its integration is at least at risk due to sepsis or the tumour. Once the sepsis has subsided or the convalescence has progressed far enough after tumour removal, a new implant can be implanted.

The sepsis or tumours may, depending on the severity, make it necessary to dissect a more or less large area of the surrounding bone tissue. As a result, a part of the supporting apparatus is missing after such explantation, which results in a shortening of the surrounding soft tissue without corresponding replacement. However, a direct reimplantation to prevent such an effect is not possible. On the one hand, the septicaemia must completely subside, on the other hand it is difficult to predict which kind of prosthesis can be implanted thereafter because of the section of bone tissue. In addition, the section may initially require a build-up of bone tissue.

In the treatment of sepsis, the patient is immobilized, while said sepsis is combated through the use of medicines, in particular antibiotics. The immobilization of the patient not only leads to a shortening of the surrounding soft tissue, but also to a strong weakening of the muscle tissue. Usually, physiotherapeutic measures are carried out before an implantation of an endoprosthesis in order to strengthen the muscle tissue as well as the ligament apparatus. However, this is only possible to a very limited extent after explantation of the prosthesis and subsequent immobilization and reduces the chances of success of the new endoprosthesis after revision.

In order to prevent the shortening of the soft tissue, a method has therefore been developed in which the cavity produced by the explantation is partly filled by bone cementation. For this purpose, the bone cement stirred in the operating room is adapted in the still plastic state to the cavity to be filled. In order to ensure an optimal adaptation of such a bone cement spacer, this is carried out at least partly by modelling on the remaining bone tissue of the patient. However, since the bone cement in the plastic state has not yet cured and thus an endothermic curing reaction further takes place in it, the risk of damage to the surrounding tissue exists as a result of too high temperatures. Thus, the thermal energy emitted by the bone cement can lead to necrosis of the surrounding bone tissue.

However, the patient must continue to be immobilized also when using a bone cement spacer, since its material properties and the mechanical connection to the remaining bone tissue are insufficient despite the modelling. The bone cement is essentially a material which occupies the space of the dissected bone but is not mechanically capable of enabling the patient to be mobilized.

The volume or the thickness of the material of such a spacer also plays a role, which causes variations in the mechanical properties as well as the dimensions of the bone cement spacer during curing. As a result, a bone cement spacer can thus provide neither the support function nor the mobility of the explanted joint replacement. It follows that at least the weakening of the muscle tissue and of the ligament apparatus cannot be counteracted even when a spacer is used. This has a negative effect, particularly in the case of a longer dwell time of the spacer in the patient from several weeks to months.

SUMMARY OF THE INVENTION

It was thus the object of the invention to provide a solution which promotes the mobility of a patient, in particular in the interests of a favourable healing process. It was a further object of the present invention to reduce the operating time, which is extended in particular by the preparation of the spacer. In addition, it was an object to replace the bone cement spacers with a solution which does not have any adverse effects caused by the heat development described above.

This object is achieved by the combination of features defined in claim 1. The dependent claims describe preferred embodiments of the present invention.

In order to achieve this object, the present invention provides a modular interim joint prosthesis as a replacement for an explanted joint endoprosthesis. The interim joint prosthesis can be inserted into a long bone and has a main body with a main-body coupling segment and a shaft having a shaft coupling segment. In this case, the shaft coupling segment can detachably be coupled to the main-body coupling segment.

The term "can be inserted into a long bone", as used herein, illustrates that after the removal of the previously implanted joint endoprosthesis, in the event of a necessary revision, for example due to sepsis, the interim prosthesis is used instead of the removed, i.e. explanted, prosthesis and engages for this purpose partly into the remaining long bone. The interim prosthesis is thus fixed in the body of the patient in such a way that it penetrates the medullary canal of the long bone instead of the actual endoprosthesis.

The modular design of the interim joint prosthesis, due to its components that can be coupled, allows an individual adaptation of the prosthesis to the patient, which is an advantage over the conventional interim solutions, in particular cast cement prostheses. In contrast to "permanent" endoprostheses, individual adaptation is not restricted to the prosthesis shaft and the joint head. Compared to these "permanent" endoprostheses, the prosthesis shaft is thus divided into a main body and a shaft.

In a preferred embodiment of the invention, the modular interim joint prosthesis is made of plastic and/or metal. This provides the interim joint prosthesis with increased strength over conventional cement prostheses. If the interim joint prosthesis or individual components thereof are made of metal, the metal preferably contains iron or titanium.

In one embodiment of the invention, the interim prosthesis consists, for example, of steel. In the case of steel, the interim joint prosthesis or the individual components thereof preferably comprise a coating of titanium nitride (TiN), or titanium niobium nitride (TiNbN). Such a coating prevents the release of nickel and/or chromium, which can occur in steel deposits, thus preventing the occurrence of allergies.

In a further embodiment of the invention, the interim joint prosthesis or the individual constituents contain silver in their surface regions, as a result of which an antimicrobial effect is achieved.

The surfaces of the interim joint prosthesis or its individual components can be designed to be antiadhesive in order to suppress ingrowth of tissue or bone material. In the case of titanium, anodization can prevent the formation of titanium oxide. Titanium oxide can promote the ingrowth of tissue or bone material in surface areas. If the interim joint prosthesis or individual components thereof are made of ferrous metals such as steel, a coating with an antiadhesive silicone-containing layer, for example Teflon, is preferred. Regardless of the material, an anti-adhesive surface of a component can also be achieved by a smooth or polished surface. The average roughness $R_a$ should not exceed 0.8 µm.

Furthermore, it is conceivable to provide the interim joint prosthesis of the present invention in whole or in part with an antibiotic-containing coating. For this purpose, a suitable antibiotic can be mixed into a matrix before the antibiotic-containing matrix is subsequently applied to the surface of the prosthesis or to surface areas thereof. Cement-containing compounds having a sufficient viscosity such as bone cement are used for example as a matrix.

Corresponding matrix systems can also be used to compensate for small differences in the volume of the interim joint prosthesis compared to the explanted endoprosthesis and/or for filling existing cavities, i.e. for modulating purposes. The latter can be carried out during manufacture or also before the operation, as well as a coating of the interim prosthesis or components thereof with this material. Thus, the generation of heat damage can be prevented. The preferred use of metal for the interim prosthesis also avoids heat damage due to its thermal conductivity when compensating for differences in volume.

A fundamental advantage of the modular interim joint prostheses is therefore that these prostheses are already manufactured before their use, i.e. prior to the intervention on the patient. Consequently, interim joint prostheses according to the invention thus differ from prior art systems, which in the course of an operation are cast or modelled from bone cement for example, i.e. a multi-component polymer. A major disadvantage of such conventional systems is the above-described heat development, which begins due to chemical reactions during the modulation phase. This can cause damage to the body tissue which is avoided with the systems of the present invention.

Because of the higher strength, the modular interim joint prosthesis also has an increased load-bearing capacity compared to conventional interim prostheses, thereby enabling the mobility of the patient during the period during which the interim prosthesis replaces the actual endoprosthesis.

A main body of the modular interim joint prosthesis replaces at least a part of a joint, in particular a femoral neck portion of a hip or a knee joint or the femoral or tibial part hereof.

In other words, the main body represents a placeholder or spacer which holds the tissue of the patient approximately in its original position. In this case, the main body preferably forms the geometry of the replaced joint or joint section and/or approximately the cross-sectional geometry of the dissected bone in a plane which is approximately perpendicular to the longitudinal direction of the bone, thus preventing shrinkage of the surrounding tissue, including the outer skin layers. The result is that the remaining body tissue, after the healing and removal of the interim prosthesis, can then easily accommodate the permanent replacement again, i.e. the actual endoprosthesis.

In a preferred embodiment of the invention, the main-body coupling segment is designed to be complementary to the shaft coupling segment. In further preferred embodiments of the invention, the main body at least partially replaces a part of the metaphysis and/or the main body is supported on the diaphysis or the meta-diaphyseal region of a long bone.

In a particularly preferred embodiment of the present invention, the main body of the interim joint prosthesis has at least two clamping wings, which are displaceable relative to the main body in a substantially perpendicular direction to the shaft, wherein each clamping wing has a stop which extends at least on one side of the main body in the longitudinal direction of the shaft beyond the main body.

Due to the displaceability of the stops or clamping wings, fixing of the main body to the bone is enabled independently of the position of the shaft. The clamping wings thereby prevent a rotation of the main body about the longitudinal axis of the shaft.

Preferably, the clamping wings for clamping are arranged diametrically in a plane which is perpendicular to the longitudinal direction of the shaft. Particularly preferably, the clamping wings are displaceable independently of one another so that the stops of the clamping wings can be in contact with the diaphysis or the meta-diaphyseal region of a joint at different distances from the shaft.

In a further preferred embodiment of the present invention, the clamping wings can be displaced via at least one, preferably two, telescopic rods. By means of this preferred embodiment, a simple construction of the interim joint prosthesis is ensured, and the use of two telescopic rods per clamping wing prevents rotation of the clamping wing relative to the main body. In a further alternative embodiment of the invention, a rotation of the clamping wing relative to the main body can be countered by using a telescopic rod with a non-rotationally symmetrical cross-section.

In a further, also particularly preferred embodiment of the present invention, at least one telescopic rod of at least one clamping wing has an anti-slip device.

This anti-slip device is preferably designed as a recess in the longitudinal direction of the telescopic rod, into which a clamping wing fixing element of the main body engages. This prevents the clamping wing from falling out, which is particularly advantageous when aligning the main body after the insertion of the modular interim joint prosthesis into the patient.

The engagement of the clamping wing fixing element into an anti-slip device designed as a recess ensures displacement of the telescopic rod as far as the outer ends of the recess, which act as stops. The clamping wings are only fixed once the clamping wing fixing element has been fixed in its position.

In a preferred embodiment of the invention, the main-body coupling segment of the main body of the interim joint prosthesis is a through-hole, in which the shaft is displaceably arranged and preferably can be fixed via a shaft fixing element. This ensures an accurate adaptation of the interim joint prosthesis via the fixing element to a dissected bone. An exact adaptation of the interim joint prosthesis is achieved at least not only exclusively by the selection of the shaft length, but also by the possibility that the shaft is displaced in the through-hole. In this case, the shaft can protrude on both sides of the main body and be implanted in sections of adjoining long bones, i.e. they can reach into said bone.

In a further preferred embodiment of the present invention, the shaft has an engagement segment for a coupling tool at least along a section of its length formed by at least two parallel opposing surfaces. This ensures an engagement of a coupling tool, preferably a wrench, over the entire segment.

Particularly preferably, the segment extends over at least half or essentially over the entire length, but at least over 80% of the shaft length. In interaction with the shaft fixing element or, in the case of a corresponding cross-sectional shape of the hole, a flattened section can also serve as an anti-rotational element. This is obviously not only the case for a through-hole, but also for a blind hole.

In another particularly preferred embodiment of the present invention, the main body of the interim joint prosthesis has a joint linkage segment on which a joint member can be detachably fixed with its joint coupling segment.

The joint linkage segment permits the coupling to a joint part, resulting in a mobility of the interim joint prosthesis. This is associated with a gain in quality of life for the patient. Particularly preferably, the joint coupling segment is arranged on the side in the longitudinal direction of the main body which is opposite the side from which the shaft protrudes.

The joint linkage segment and the joint coupling segment can be formed in a frustoconical manner. For simple (dis)mounting, the cone angle can be selected to be larger than for normal prosthesis connections, so that a lower self-locking effect of the cone connection is achieved.

In a preferred embodiment, a joint fixing element, e.g. in the form of a screw, is provided on the joint part in the region of the joint coupling segment, which can fix the joint part on the joint linkage segment.

In the case of a cone connection, the joint fixing element is preferably arranged in such a way that the cone connection is compressed by fixing the joint fixing element, e.g. by tightening a screw.

The main body is preferably formed in an angular manner. For the use of the modular interim joint prosthesis according to the invention as a hip endoprosthesis, the joint linkage segment (28) preferably stands at an angle of 135° to the shaft (60). The main body is essentially formed in this case as a femoral neck region, which is supplemented modularly by shaft elements to form a hip prosthesis.

If the modular interim joint prosthesis is essentially used as a placeholder, for example for an artificial knee joint or a femoral or tibial part thereof, then the joint body is essentially cylindrical and, as described above, forms approximately the cross-section of the explanted joint or roughly the cross-section of the bone in this region.

In a further preferred embodiment of the invention, the interim joint prosthesis has two main bodies. The two main bodies of such a preferred interim joint prosthesis can replace two joints, i.e. two artificial joints, which had to be removed from a patient, and are preferably connected to one another via at least one shaft.

Such an interim joint prosthesis thus permits replacement also in cases where a conventional bone cement placeholder could no longer be used. For example, interim joint prostheses of such a preferred embodiment may replace a major part of a long bone, if not even an entire long bone. In a preferred embodiment of the invention, the interim joint prosthesis therefore concerns a temporary replacement for a hip and knee joint.

In a further embodiment of the invention, the interim joint prosthesis further comprises a shaft with a support or a support shaft, wherein the support shaft has a distal end and a proximal end, between which a support flange is arranged which extends radially outwards from the support shaft. The support shaft has a diameter which is greater than the at least one shaft coupling segment and is dimensioned such that it can rest on a dissected cross-section of the long bone. The support shaft is intended in particular for the area of the diaphysis. In other words, the support shaft allows good support of the interim joint prosthesis on a long bone and prevents too much penetration of the shaft into the long bone.

In a further preferred embodiment of the invention, the shaft (60) and the support shaft (70), at their proximal and distal ends, comprise mutually facing complementary threads or thread connectors as well as at least one engagement segment for a coupling tool. By means of this preferred embodiment of the interim joint prosthesis according to the invention, it is ensured that different shafts and different main bodies can be combined with one another. The coupling segment of the main body can be a through-hole for this purpose or provided in the form of a female or male thread. These connecting elements are, in a preferred embodiment of the invention, a male connecting element on one side of the shaft and a female connecting element on another side of the respective shaft or main body. Threaded connectors are understood by the present invention to be both connecting elements with a thread as well as with a bayonet closure.

The aforementioned coupling tool for tightening the threaded connectors is preferably a wrench with engaging surfaces that are parallel to each other.

In a further embodiment, the present invention relates to methods for treating a patient with a joint endoprosthesis, comprising the steps of: (i) removing the joint endoprosthesis from the patient; and (ii) inserting an interim joint prosthesis as described herein. The method further preferably comprises the step (iii) of removing the interim joint prosthesis.

The modular interim joint prosthesis as described herein serves as an interim replacement of an endoprosthesis in a patient, preferably a human being. The present invention also relates to methods for the surgical and/or therapeutic treatment of a human or animal body, in which an existing joint endoprosthesis is first removed and is subsequently replaced for a period of time by the interim joint prosthesis described herein. The method of surgical or therapeutic treatment is ideally suitable in patients with acute sepsis in the area of the joint endoprosthesis.

BRIEF DESCRIPTION OF THE DRAWINGS

With the aid of the following figures and description, embodiment examples for better understanding of the present invention are discussed in detail. For this purpose, the features shown in the figures are marked with reference numerals. In the case of different embodiment examples, the same reference numerals are used, provided that the features in these embodiment examples are the same or have the same effect.

DETAILED DESCRIPTION OF PREFERRED EMBODIMENTS

Figure 5:
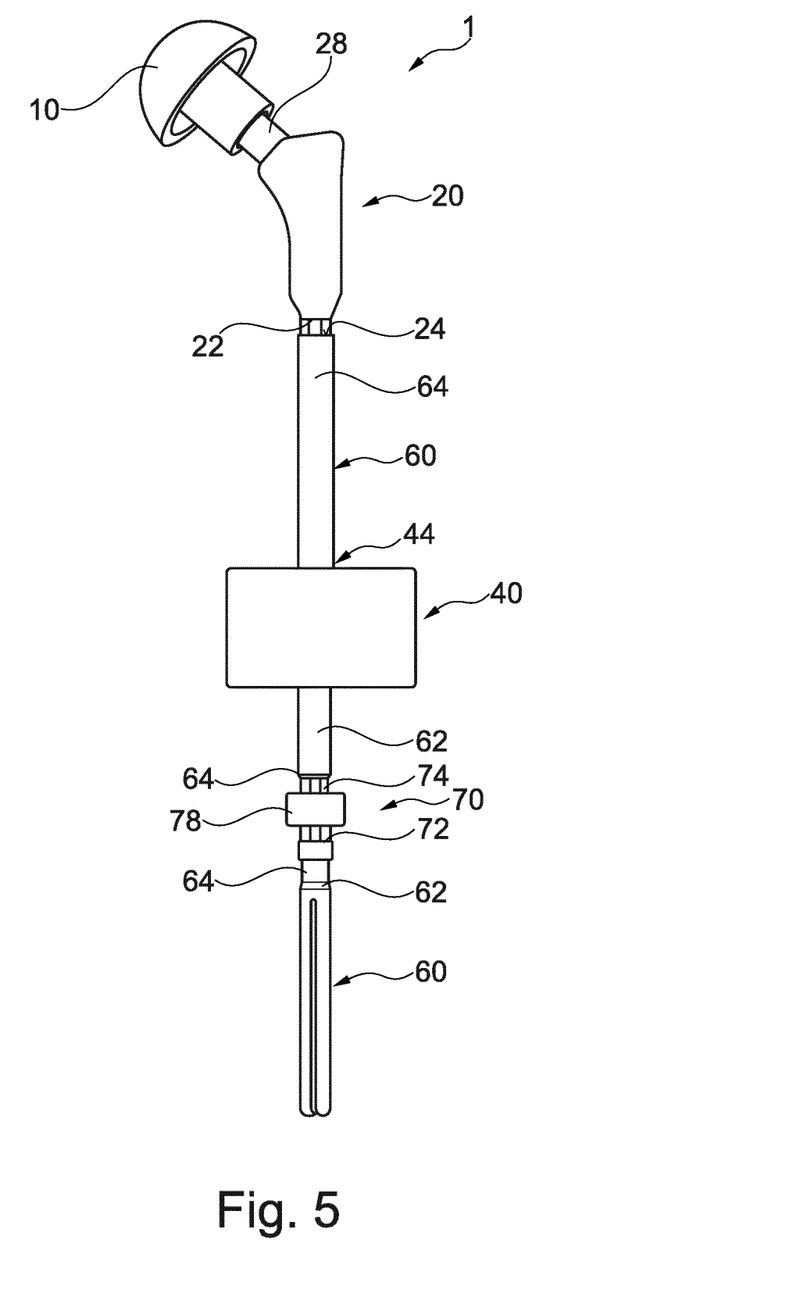
FIG. 5 shows a modular interim joint prosthesis according to the invention with two main bodies.

FIG. 5 shows an example of a structure of a modularly arranged interim joint prosthesis 1 according to the invention, which is provided for replacing an explanted joint endoprosthesis (not shown). The interim joint prosthesis 1 has two main bodies 20, 40. Thus, in the design of this interim joint prosthesis 1, an embodiment is concerned which is provided for the replacement of two explanted artificial joints. In the specific case shown in FIG. 5, this is a replacement of a hip prosthesis and a knee joint.

As can be recognized with respect to the interim prosthesis 1 shown in FIG. 5, it provides the patient with a certain degree of mobility since the joint part 10 is guided in the acetabulum, which is not shown, and thus retains its function as a joint. On the other hand, the main body 40, which serves as a substitute for an explanted artificial knee joint, is flexurally stiff and thus does not permit any articulated movement. However, the patient can move his leg out of the hip thanks to the joint part 10 located on the main body 20. As a result, the embodiment of an interim joint 1 shown in FIG. 5 allows, on the one hand, physiotherapeutic measures and, on the other hand, this design provides the patient with a certain degree of freedom of movement. This has a positive effect on the muscles and ligaments.

At the same time, the main body 20, as also the main body 40, ensures that the surrounding soft tissue is unable to shorten to such an extent, neither in the longitudinal direction of the leg nor in the transverse direction thereof. Thus, a new implantation of a permanent joint replacement is not prevented.

The main body 20 replaces the angled region of the femur in the region of the femoral neck. For the interim prosthesis according to the invention, an angle of 135° is preferably selected.

Figure 4:
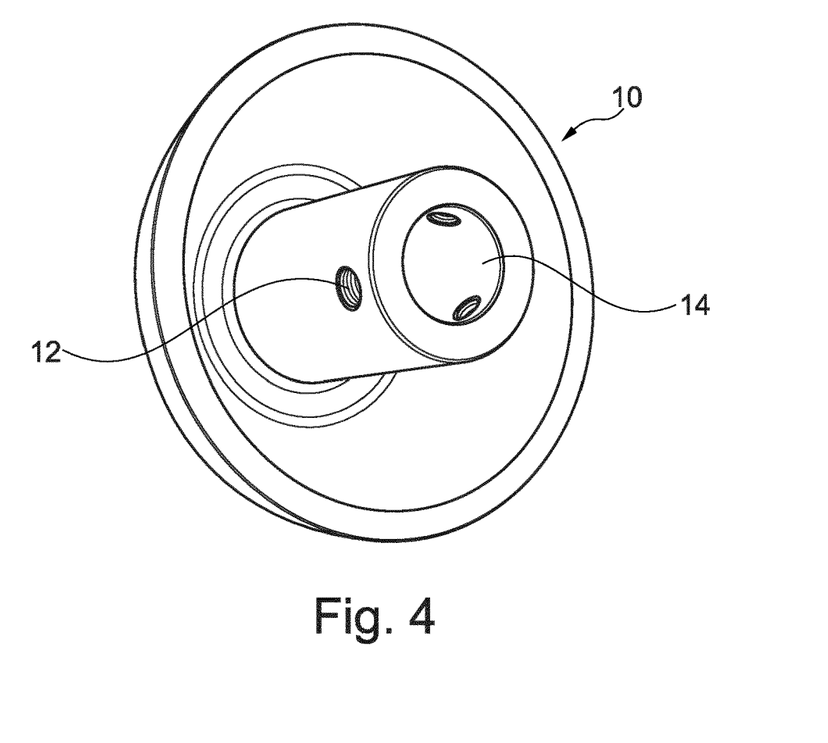
FIG. 4 shows a joint part, which can be fixed to a main body of the interim joint prosthesis by means of a joint coupling segment.

If a main body 20, 40 has a joint part 10, a joint linkage segment 28 is then provided for its attachment to the main body 20, 40. Said joint linkage segment is preferably conical and has already been explained above. Consequently, in such an embodiment, the joint part 10 has a conical inner surface 14 (FIG. 4).

Furthermore, at least one joint fixing element 12 can be provided on the joint element 10 in order to fix the joint element 10 to the joint linkage segment 28 of the main body 20. Advantageously, the at least one joint fixing element 12 is arranged in such a way that its fixing or tightening presses the conical joint linkage segment 28 into the corresponding joint coupling segment 14 of the joint part 10 and thus ensures a play-free connection. This can be done, for example, by means of a tapered screw as a joint fixing element 12 and a correspondingly pointed recess in the surface of the joint linkage segment 28. If more than one joint fixing element 12 is provided, then these are preferably evenly distributed around the circumference of the joint coupling segment.

In order to couple the main body 20, 40 to a shaft 60, two attachment possibilities are particularly preferred in the present invention. In the first attachment possibility, the main body 20, 40 has a main-body coupling segment 24, 44 in the longitudinal direction at least one end. In this case, the main-body coupling segment 24, 44 preferably comprises a thread for connecting. In the context of the invention, this also includes a bayonet. On the shaft coupling segment 64, which is complementary thereto, of a shaft 60 which can be connected to the main body 20, 40 a complementary thread is accordingly disposed, so that the main body 20, 40 and the shaft 60 can be coupled to one another.

In order to tighten the connection between a shaft 60 and a main body 20, 40, an engagement segment 22 is preferably provided on the main body 20, 40 and an engagement segment 62, 72 on the shaft 60, 70. As described above, the engagement segment can be provided over essentially the entire length of the shaft 60, but at least over 50%, 60%, 70%, 80%, and preferably at least 90%.

The engagement segment 22, 62, 72 additionally preferably concerns two mutually parallel engagement surfaces 65 (FIG. 6), into which a coupling tool 2 can engage. In the embodiment example shown, the coupling tool 2 is designed in the form of a wrench.

If a coupling segment is located in the longitudinal direction at both ends of a main body 20, 40 and/or a shaft 60, 70, the coupling segment of the one side is complementary to the coupling segment on the other side. In the case of a thread, the external thread is accordingly located on one side of the main body 20, 40 or of the shaft 60, and the inner thread on the respective other side of the main body 20, 40 or of the shaft 60. Consequently, the shafts 60, 70 and main bodies 20, 40 can be interchanged as desired.

Figure 7:
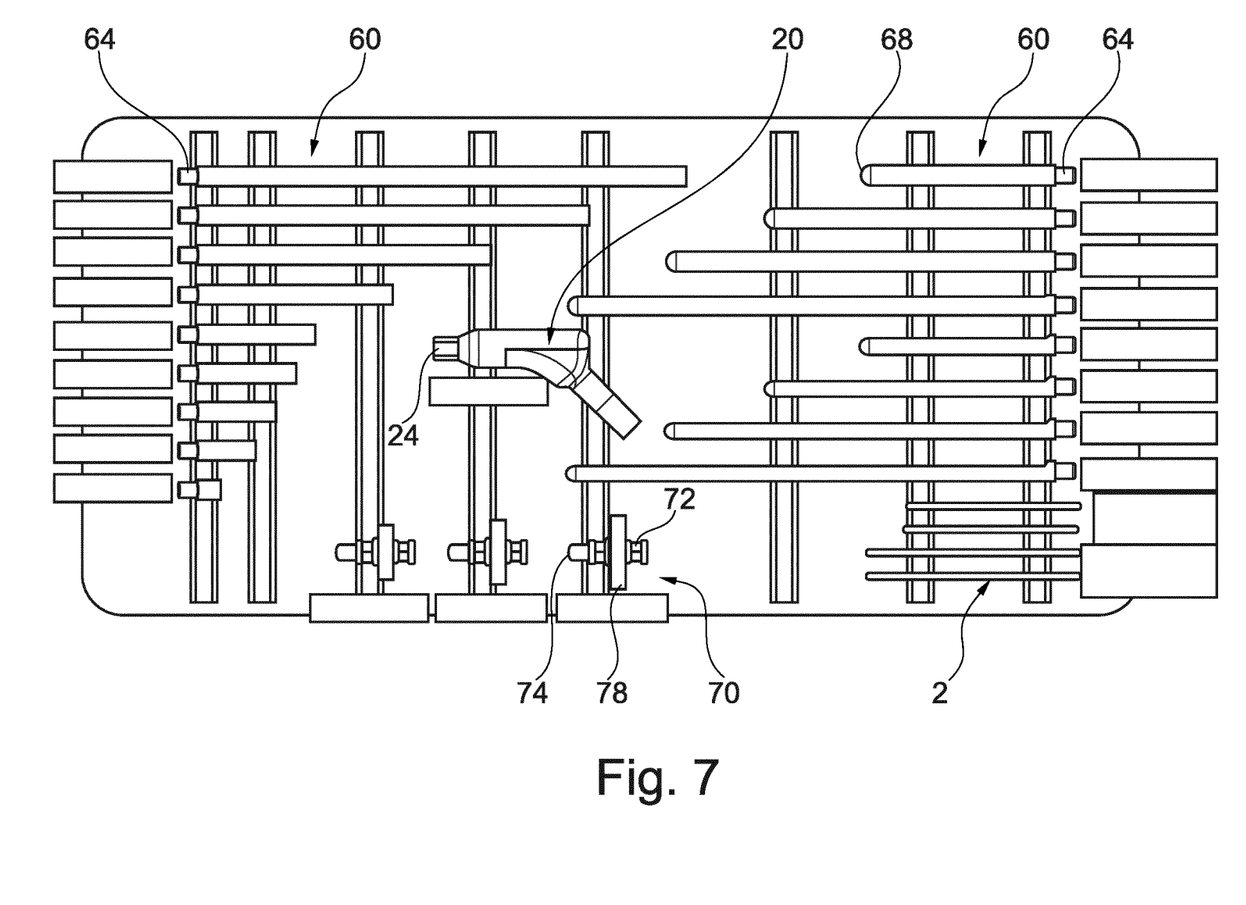
FIGS. 7 and 8 each show a set of different components of the modular interim joint prosthesis as described herein.
Figure 8:
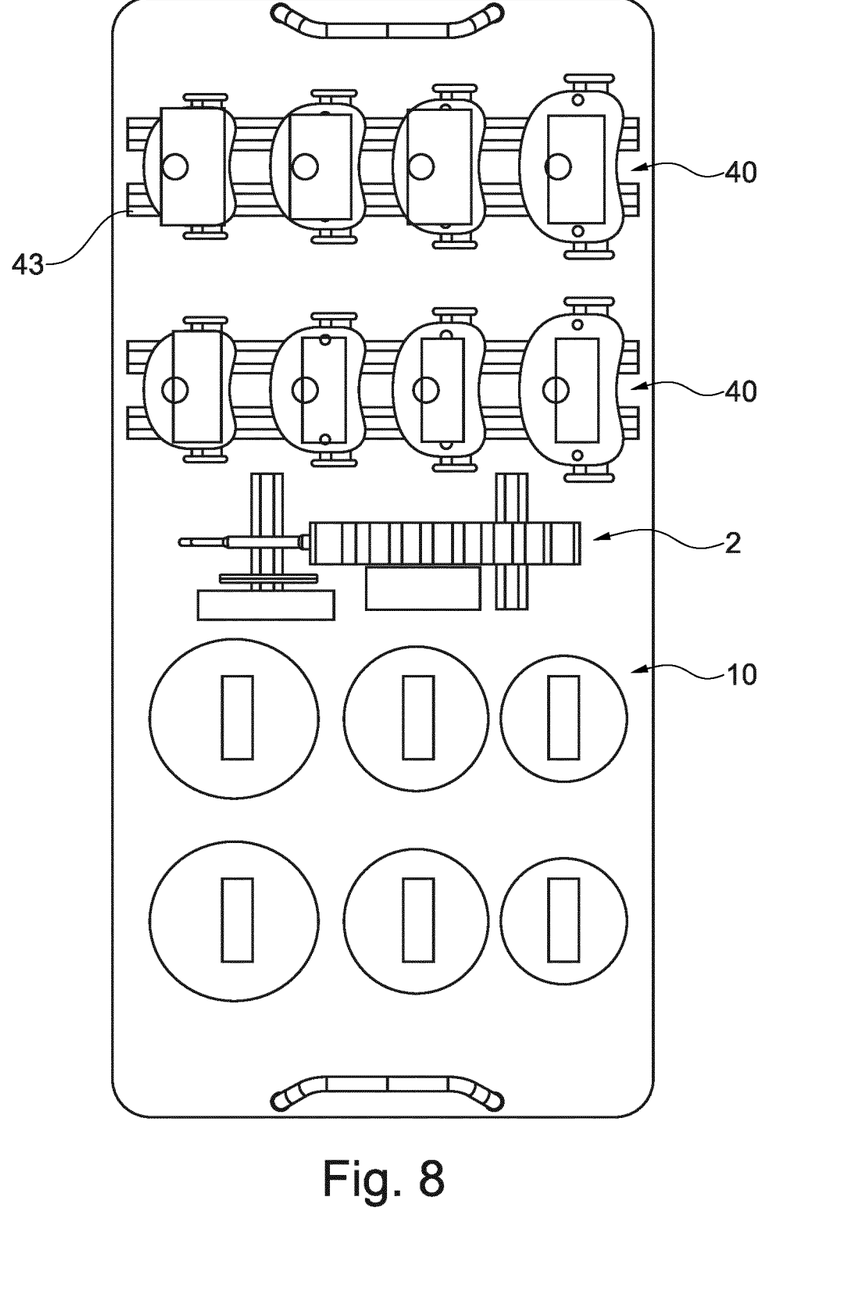

With reference to FIG. 7, this is shown for the shaft 60 and the support shaft 70. Thus, on the one side of the shafts 60, 70, the male coupling segment 64 and 74 is shown. The complementary female coupling segment 64, 74 on the opposite side of the shafts 60, 70 is located in the end face of the shafts and is not visible in FIG. 7.

In the second attachment possibility, a hole 44 is provided in the main body 20, 40 on at least one side, into which the shaft 60, 70 can be inserted. As described above, the hole 44 is preferably a through-hole (see also FIGS. 1, 3, 6 and 8). A shaft 60, 70 can then be fixed via at least one shaft fixing element 43.

Figure 6:
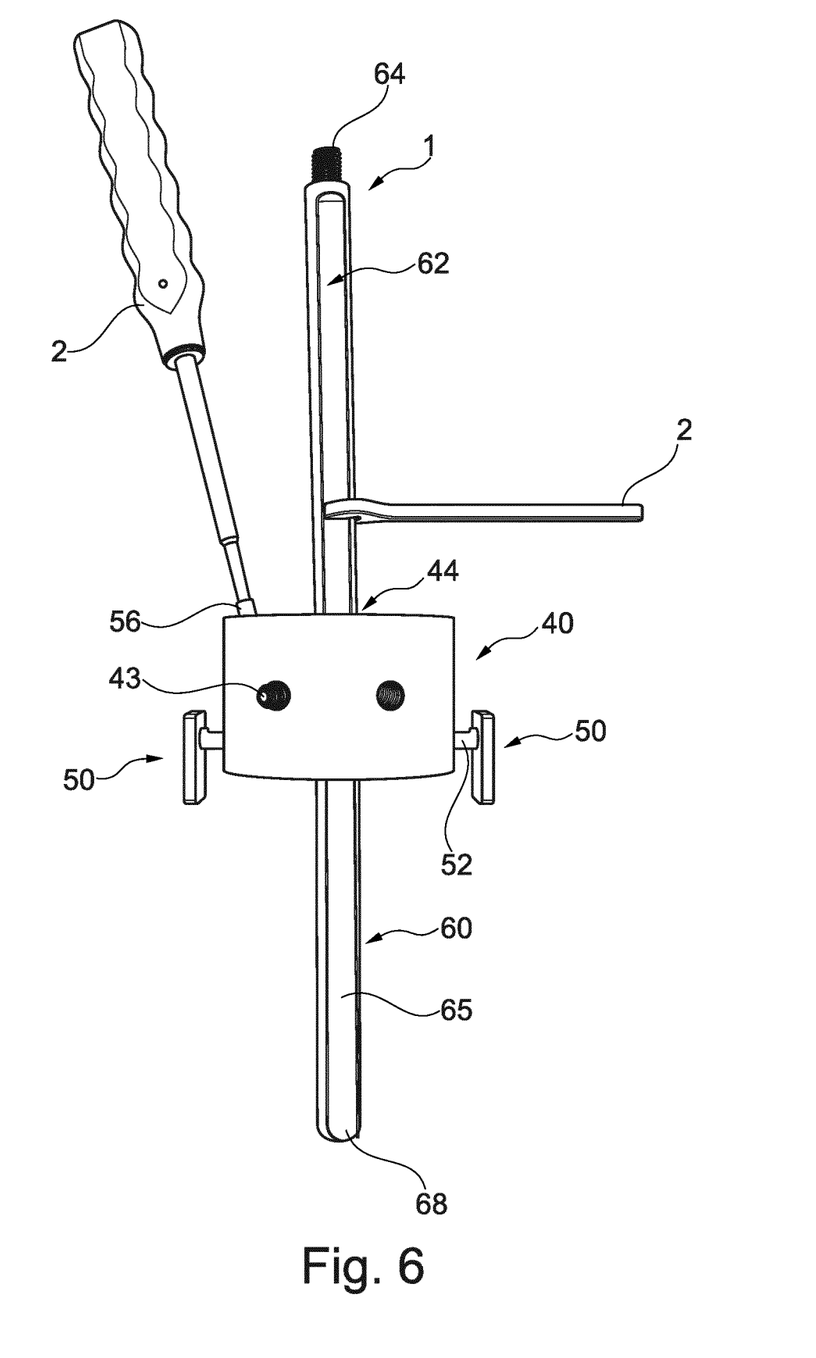
FIG. 6 shows a shaft and a main body connected to this shaft.

If a through-hole 44 is concerned, the shaft 60 can protrude on both sides from the main body 20, 40 (FIGS. 5 and 6). Such an arrangement is shown both in FIG. 5 and in FIG. 6. In both figures, a main body 40 is provided as a replacement for an artificial knee joint. In these cases, the same shaft 60 protrudes in the longitudinal direction on both sides from the main body 40.

As a result, it is possible to insert the shaft 60, which is inserted into the through-hole 44, into the two adjacent long bones and to thus fix the main body 40 laterally. If the main body 40 is provided, for example, for the replacement of an artificial knee joint, one side of the shaft 60 is located in the femur, while the other side of the shaft 60 is arranged in the tibia. Such a case is shown in FIG. 5. The displaceability of a shaft 60 in the main body 20, 40 due to a through-hole 44 has the advantages already described above.

In the embodiment example shown in FIG. 5, although the shaft 60 inserted into the through-hole 44 of the main body 40 is possibly provided for the purpose of being introduced into sections of a long bone, it is not provided for securing the interim prosthesis 1 laterally. Instead, the interim prosthesis 1 shown in FIG. 5 is provided for a case in which the entire femur has been removed, as is the proximal part of the tibia. As a result, none of the main bodies 20, 40 are supported with their surfaces oriented in the longitudinal direction on a long bone.

In order to nevertheless permit a certain amount of anchoring in a long bone, the interim prosthesis 1 can be inserted via its shaft 60, which is attached at the distal end, into the distal end of a tibia (not shown). In order to prevent slipping through of the shaft 60, a support shaft 70 is provided, which is inserted via the above-described complementary connectors 64, 74 between the two shafts 60. The support flange 78, which extends radially outwards, of the support shaft 70 then lies on the proximal sectional surface of the tibia, thus assuming the role of the aforementioned surfaces of the main bodies 20, 40, and thus prevents slipping through. Since the interim prosthesis 1 shown in FIG. 5 is provided for the aforementioned case, the main body 40 does not have any of the clamping wings 50 already described above and in more detail below.

If, on the other hand, a shaft 60 protrudes only on one side of a main body 20, 40, the interim prosthesis is used only for the replacement of a joint side of an artificial joint that was previously explanted. In FIG. 5, the main body 20 would thus replace only the femoral part of the hip joint when the shaft 60 is attached via a hole. The same applies to the replacement of the tibial or femoral part of a knee joint. In the case of a one-sided replacement, the main body 40 has a correspondingly shorter length.

In general, for the main body 40, which is provided in the shown embodiments for the replacement of a knee joint (FIGS. 5 and 6) or of the tibial part of a knee joint (cf. FIGS. 1 to 3), the length thereof is provided in a range from 10 to 80 mm. The dimension of the main body 40 in the illustrated embodiments is provided in the lateral direction in the range between 40 and 90 mm and in the direction perpendicular to it in the range between 35 to 55 mm.

The shaft preferably has a cross-section which remains constant over its length. The term "essentially" includes possibly existing engagement surfaces 62, as shown in FIG. 6. The cross-section of the shaft 60, however, is designed such that it can be inserted or passed through the diaphyseal region of a long bone. For this purpose, the shaft 60 has a diameter of 8 to 15 mm, preferably 10 to 12 mm.

Figure 1:
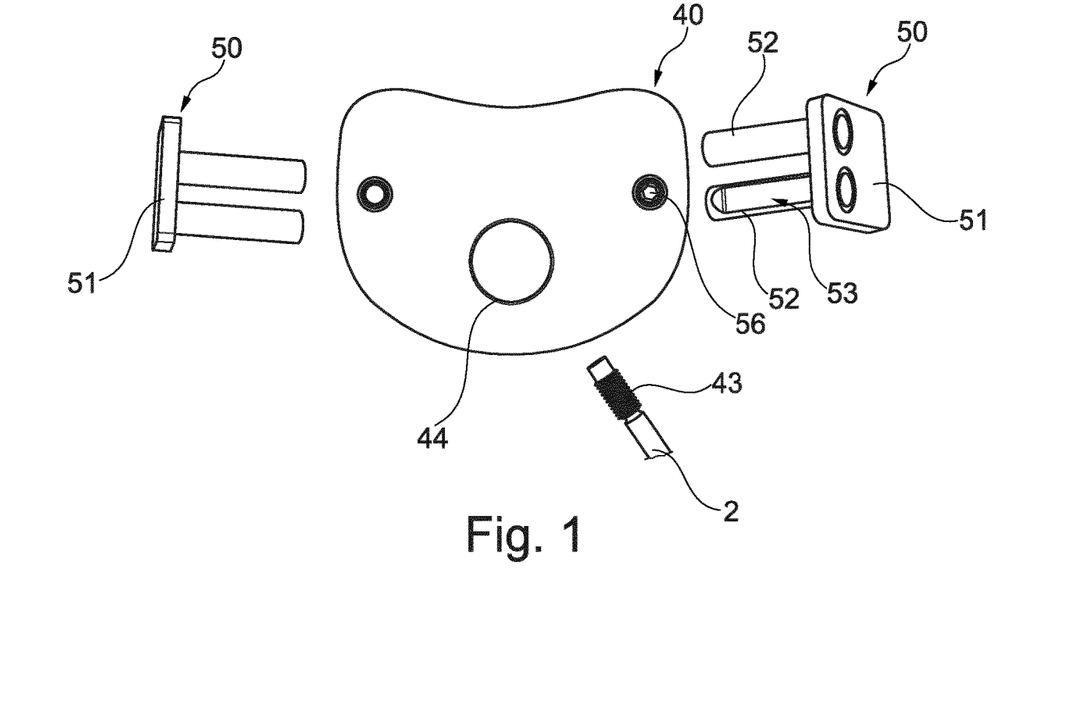
FIG. 1 shows a main body of the interim joint prosthesis according to the invention for a knee (femur and/or tibia), which has two clamping wings with stops.
Figure 2:
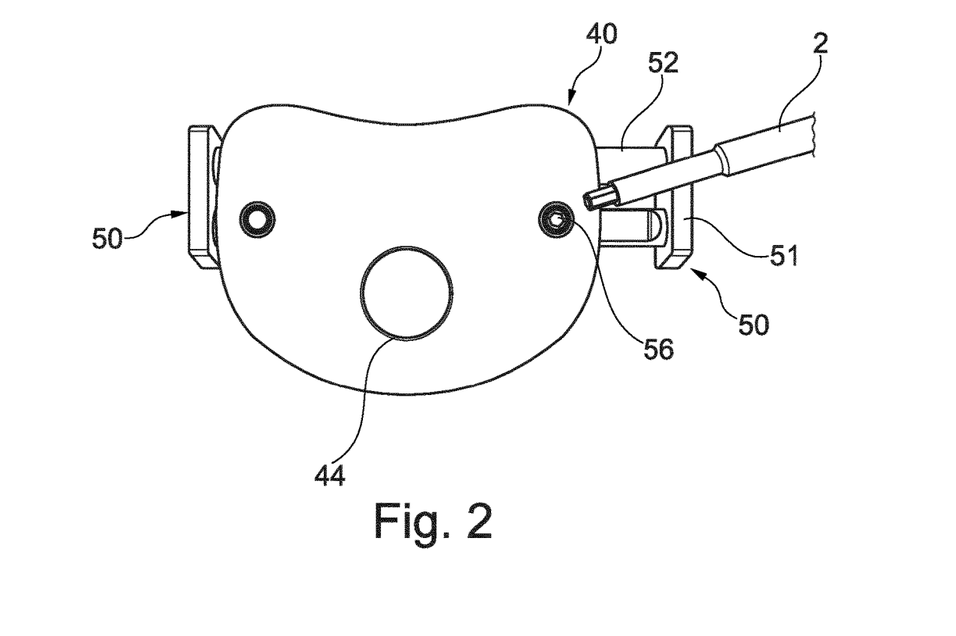
FIG. 2 shows the main body in an enlarged view with clamping wings inserted.

The main body 20, 40, in accordance with the present invention, is characterized in that, on the contrary, it can preferably not be inserted into the diaphyseal region of the adjacent long bone. In the cross-section perpendicular to its longitudinal direction, the outer contour of the preferably cylindrically shaped main body 40, in its preferred embodiment, essentially follows the outer shape in the metaphyseal region of a tibia in the same joint section, as a replacement for at least a part of a knee joint (FIGS. 1 and 2).

A main body 20, 40 can also have clamping wings 50 (FIGS. 1 to 3 and 6). Relating to the cross-section of the main body 40, the clamping wings 50 are arranged perpendicularly to the longitudinal direction thereof, preferably (diametrically) opposite.

In one embodiment, they are guided by means of a telescopic rod 52, which is displaceably arranged in an opening or a hole in the main body 40. Thus, a clamping wing 50 can be pulled out of the main body 40 in the manner of a clamping jaw as in the case of a vice, and pushed into it.

Figure 3:
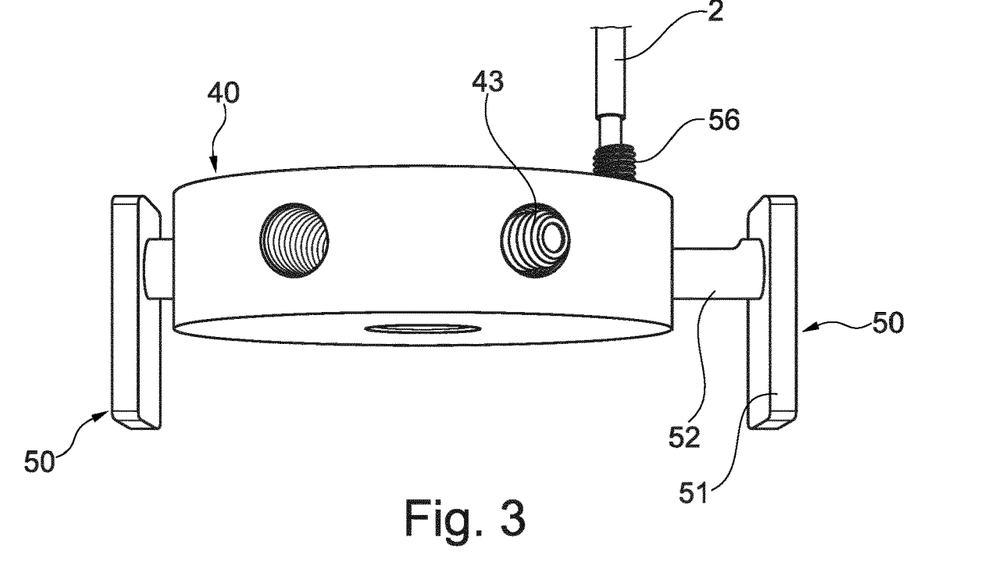
FIG. 3 shows a front view of the main body.

As can be seen in FIG. 3, the clamping wing 50 has a stop region 51 which, in the inserted state of the interim prosthesis 1, strikes the adjacent long bone with its surface facing the main body 40. Since this applies to both opposing clamping wings 50, the intermediate region, i.e. preferably the metaphyseal region, is clamped. In this case, the interlocking connection produced by the part of the stop region 51 which projects beyond the main body 40 in the longitudinal direction of the main body 40 with the circumference of the abutting long bone secures the main body 40 against a rotation about its longitudinal axis.

After their adjustment, the clamping wings 50 are fixed in the main body 40 by the clamping wing fixing element 56. Furthermore, an anti-slip device 53, which was already described above in closer detail, can be provided in the clamping wings 50, which in the embodiments shown in FIGS. 1 to 3 is designed as a recess formed in the longitudinal direction of a telescopic rod.

The extreme end of a shaft 60 can be formed as a rounded end segment 68 (FIGS. 5 to 7).

In all embodiments according to the invention, the interim prosthesis allows a patient-specific solution due to its modular design. Due to their mechanical load-bearing capacity and also their flexibility, which depends on the respective design, a patient is further provided with restricted mobility. This has a positive effect on the quality of life of the patient during the illness phase and also improves the preparation and thus the success prospects of a revision.

LIST OF REFERENCE NUMERALS

1 Interim prosthesis
2 Coupling tool
3 Joint part
4 Joint fixing element
14 Joint coupling segment
20 Main body
22 Engagement segment for coupling tool
24 Main-body coupling segment for a shaft
28 Joint linkage segment
40 Main body for knee
43 Shaft fixing element
44 Main-body coupling segment
50 Clamping wing
51 Stop
52 Telescopic rod
53 Anti-slip device
56 Clamping-wing fixing device
60 Shaft
62 Engagement segment for coupling tool
64 Shaft coupling segment
65 Engagement surface of an engagement segment 62
68 Rounded end segment
70 Support shaft
72 Engagement segment
74 Coupling segment of the support shaft
78 Support flange

The invention claimed is:

1. An interim joint prosthesis configured to be inserted into a long bone and used for a replacement of a joint endoprosthesis to be explanted, said interim joint prosthesis comprising:
(i) a main body arranged to be supported on the long bone and configured as a placeholder for a joint section of the joint endoprosthesis to be explanted, wherein the main body comprises a main body coupling portion, the main body coupling portion being a through-hole, and further comprising at least two clamping wings which are displaceable perpendicular to a longitudinal direction of the main body relative to the main body, and
each of the at least two clamping wings comprises a stop which extends in the longitudinal direction of the main body at least on one side of the main body beyond the main body;
(ii) an integrally formed shaft comprising a shaft coupling portion and a longitudinal axis, wherein a portion of the shaft, the portion having a constant cross-section, is slidably arranged in the through-hole along the longitudinal axis of the shaft, whereby the shaft can protrude on both sides of the main body to be implanted into sections of adjoining long bones, and (iii) a shaft fixing element configured to fix the shaft arranged in the through-hole to the main body.

2. The interim joint prosthesis according to claim 1, wherein each of the at least two clamping wings further comprises at least one telescopic rod, and each of the at least two clamping wings is displaceable via the at least one telescopic rod.

3. The interim joint prosthesis according to claim 1 or 2, wherein the main body further comprises a clamping wing fixing element, at least one of the at least two clamping wings further comprises an anti-slip device, and the clamping wing fixing element of the main body is configured to engage with the anti-slip device.

4. The interim joint prosthesis according to claim 1 or 2, wherein the shaft further comprises a coupling tool engagement segment formed on at least two parallel surfaces of the shaft arranged mutually opposite each other.

5. The interim joint prosthesis according to claim 1, further comprising:

a joint part comprising a joint coupling segment, wherein the main body further comprises a joint linkage segment, and the joint linkage segment is detachably coupled to the joint coupling segment.

6. The interim joint prosthesis according to claim 1, wherein the prosthesis further comprises a second main body, wherein the main body and the second main body are connected to one another.

7. The interim joint prosthesis according to claim 1, further comprising:

a support shaft with a distal end and a proximal end; and a support flange arranged between the distal end and the proximal end of the support shaft, wherein the support flange extends radially outwardly from the support shaft.

8. The interim joint prosthesis according to claim 7, wherein the shaft and the support shaft each comprise a coupling segment at one end, and a respective coupling segment complementary thereto at the opposing end and at least one engagement segment for a coupling tool, wherein the coupling segments comprise threads.

9. The interim joint prosthesis according to claim 1, comprising an antiadhesive, antimicrobial and/or antibiotic-containing surface or surface portions.

* * * * *